| United States Patent [19] | [11] Patent Number: 4,536,602 |
|---|---|
| Deeba | [45] Date of Patent: Aug. 20, 1985 |

[54] AMINATION OF OLEFINS USING ORGANIC ACID CATALYSTS

[75] Inventor: Michael Deeba, Allentown, Pa.

[73] Assignee: Air Products and Chemicals, Inc., Allentown, Pa.

[21] Appl. No.: 616,359

[22] Filed: Jun. 1, 1984

[51] Int. Cl.³ .................. C07C 85/02; C07C 85/18
[52] U.S. Cl. ............................ 564/485; 564/445; 564/408
[58] Field of Search ............ 564/485, 445, 408

[56] References Cited

U.S. PATENT DOCUMENTS

| 2,381,470 | 8/1945 | Teter | 260/465.3 |
|---|---|---|---|
| 2,381,709 | 8/1945 | Apgar et al. | 260/465.3 |
| 2,392,107 | 1/1946 | Teter et al. | 260/465.3 |
| 2,398,899 | 4/1946 | Teter et al. | 260/465.3 |
| 2,417,892 | 3/1947 | Teter | 260/465.3 |
| 2,422,631 | 1/1947 | Olin et al. | 564/488 |
| 2,422,632 | 1/1947 | Olin et al. | 564/488 |
| 2,479,879 | 8/1949 | Teter | 260/465.3 |
| 2,501,556 | 3/1950 | Whitman et al. | 260/465.3 |
| 2,623,061 | 12/1952 | Teter et al. | 260/465.3 |
| 2,658,041 | 11/1953 | Teter et al. | 260/465.3 |
| 3,412,158 | 1/1968 | McLain | 564/485 |
| 4,307,250 | 12/1981 | Peterson | 564/445 |
| 4,317,949 | 3/1982 | Vaughan | 568/607 |
| 4,375,002 | 2/1983 | Peterson | 564/445 |

OTHER PUBLICATIONS

Ritter, et al., "A New Reaction of Nitriles.I.Amides From Alkenes and Mononitriles", *J. Am. Chem. Soc.* 70, 4045, (1948).

Louis P. Hammett, et al., "A Series of Simple Basic Indicators", *J. Am. Chem. Soc.* 54, 2721, (1932).

*Primary Examiner*—Charles F. Warren
*Assistant Examiner*—Harry B. Shubin
*Attorney, Agent, or Firm*—Mark L. Rodgers; E. Eugene Innis; James C. Simmons

[57] ABSTRACT

The present invention involves the catalytic amination of olefins with ammonia, a primary amine, or a secondary amine using a perfluorinated organic acid catalyst.

11 Claims, No Drawings

# AMINATION OF OLEFINS USING ORGANIC ACID CATALYSTS

TECHNICAL FIELD OF THE INVENTION

The present invention relates to the catalytic amination of olefins with ammonia, a primary amine or a secondary amine.

BACKGROUND OF THE INVENTION

The earliest work relating to the manufacture of amines by the amination of olefins, particularly ethylamines by the amination of ethylene, appears to have been done by Teter, et al. as noted in U.S. Pat. Nos. 2,623,061; 2,479,879; 2,471,892; 2,381,470; 2,658,041; 2,381,709; 2,392,107 and 2,398,899. These patents show that ammonia can be made to react with olefins, e.g. ethylene to produce amine. As noted by others through improvements in the process, substantial quantities of polyamines and polyolefins were produced by the Teter, et al. catalyst which is a metal supported on a spinel-type support, silica and diatomaceous earth and the like.

Olin, et al. in U.S. Pat. Nos. 2,422,631 and 2,422,632, discloses a process for producing amines and amides by the reaction of a mono-unsaturated olefin, carbon monoxide and an amine or ammonia. The catalyst used is a combination of a dehydrating and a hydrogenation catalyst, e.g. nickel and activated alumina, copper and silica gel, etc.

Whitman, U.S. Pat. No. 2,501,556 discloses a liquid phase reaction of ammonia and ethylene in the presence of an alkali metal catalyst to form ethylamine.

Ritter, et al. in an article entitled "A New Reaction of Nitriles.I.Amides From Alkenes and Mononitriles" disclosed the reaction whereby an olefin is reacted with hydrogen cyanide in the presence of sulfuric acid to form an amide. The amide is subsequently hydrolyzed to form the corresponding amine. See J Am. Chem. Soc. 70, 4045 (1948).

McClain, U.S. Pat. No. 3,412,158, discloses a gas phase process for producing primary alkylamines from low molecular weight olefins and ammonia by carrying out the gas phase process in the presence of a noble metal containing catalyst at temperature of from 90° to 175° C., and at pressures of from atmospheric to 2,000 psig.

Peterson et al. in U.S. Pat. Nos. 4,307,250 and 4,375,002 disclose the catalytic amination of a $C_2$-$C_8$ olefin using a synthetic crystaline alumino silicate or a naturally occuring zeolite as a catalyst. Various olefins, such as ethylene, propylene, and isobutylene are reacted with ammonia or an amine in the presence of the zeolite catalyst to produce the amine product.

SUMMARY OF THE INVENTION

The present invention involves an amination reaction which comprises reacting ammonia, a primary amine, or a secondary amine with an olefin under conditions effective for amine formation. The reaction is catalyzed by a perfluorinated organic acid catalyst having a Hammett acidity value no greater than about −10.

The use of perfluorinated organic acid catalysts allow for olefins of any size to be reacted since there is no pore size limitation with these catalysts as with the aluminosilicate catalysts commonly used in the prior art. Additionally, when the amination reaction is carried out using these organic catalysts, nitriles are not formed as a product as is the case with metal-supported catalysts. The need for using hydrogen cyanide as a reactant, as taught by Ritter, et al., is also eliminated.

The perfluorinated organic acid catalysts are stabled during the amination reaction up to temperatures of about 250° C.

DETAILED DESCRIPTION OF THE INVENTION

Olefins of any size can be aminated with ammonia, or any suitable ammonia-type compound such as a primary or a secondary amine using a perfluorinated organic acid catalyst. Unlike previous processes olefin size is not a limiting factor for this reaction, however olefins having a double bonded tertiary carbon atom such as isobutylene show the greatest reactivity. One possible explanation for this greater reactivity is that the amination reaction takes place via a carbonium ion intermediate which is formed by the reaction of the acidic catalyst with the olefin. The ammonia or ammonia-type compound then reacts with the carbonium ion intermediate to form an amine. Since tertiary olefins are generally more reactive toward acids than are secondary or primary olefins, the tendency to form the carbonium ion intermediate would be greater. Also, once formed, a tertiary carbonium ion is more stable than secondary or primary carbonium ions and, hence, provide for a longer present reactive site for the ammonia-type compound. The same theory also may apply for greater reactivity of secondary olefins versus primary olefins. Therefore, for the present invention, tertiary olefins (olefins with a tertiary double bonded carbon atom) are most preferred, with secondary olefins being preferred over primary olefins.

The catalyst employed for this reaction is an organic acid catalyst. It was found that in order to effectively catalyze olefin amination, the acidity of an organic catalyst had to exceed the acidity of 100% $H_2SO_4$. This is probably due to the fact that this level of acidity is required to form the carbonium ion intermediate which is necessary for the reaction to take place. On a Hammett acidity scale it is calculated that the organic acid must have a value no greater than −10, i.e. the approximate value of 100% $H_2SO_4$. Hammett acidity is described by Louis P. Hammett, et al. in an article entitled "A Series of Simple Basic Indicators.I. The Acidity Functions of Mixtures of Sulfonic and Perchloric Acids with Water" published in the Journal of the American Chemical Society, 54, 2721 (1932).

It was found that in order to impart this high degree of acidity and stability to an organic compound to be used as a catalyst, the compound had to be at least partially fluorinated, and preferably completely fluorinated, i.e. perfluorinated. Perferably the fluorinated organic compound will contain one or more acidic functional groups. Any typical acidic functional group or mixtures of several different groups can be used, examples being carboxylic acid and sulfonic acid groups.

Perfluorinated organic solid cation exchange resins with sulfuronic acid functional groups generally exhibit the required level of acidity and are well suited for this reaction. The perfluorinated organic backbone imparts the necessary acidity to the functional groups which would not be the case with a non-fluorinated resin. The solid resin structure of this type of catalyst provides the reactants with easy access to the catalytically active site, i.e., the acidic functional groups. While a liquid resin could be used for this reaction, a solid resin is preferred. One type of perfluorinated organic solid cation exchange resin which is particularly well suited for the present reaction is a resin having a repeating structure of the general formula:

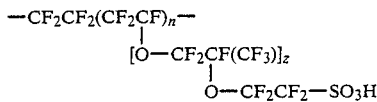

where: $n=15-20$ and $z=1$ or $2$

The resin membranes are generally five to ten mils thick and can be laminated with a polytetrafluoroethylene web to improve mechanical strength and dimensional stability. One useful catalyst for this reaction having the structure described above is H-Nafion derived from E.I. DuPont de Nemours' NAFION perfluorosulfonate polymer.

While the above resin structure is shown as having sulfonic acid functional groups, any acidic functional groups which impart a Hammett acidity value no greater than $-10$, and preferably no greater than $-15$, to the organic resin can be used, including mixtures of two or more different functional groups, such as carboxylic and sulfonic acids. It is unlikely that any solid organic resin will exhibit the required level of acidity unless it has a perfluorinated base structure, regardless of the functional groups.

Amination is generally carried out in the vapor phase at a temperature between 200° to 250° C. and a pressure between 400–2,000 psig. The perfluorosulfonic acid resins proved to be thermally unstable above 250° C. but showed good stability and catalyst life up to that temperature. The amine (or ammonia) to olefin mole ratio of the feed should be between 0.5:1 to 6:1 with a range of 1:1 to 2:1 being preferred.

The gas hourly space velocity (GHSV) of the feed should be between 300 to 4,000 with a range of 500 to 2,000 being preferred over a catalyst concentration of about 3 c.c.

PREPARATION OF H-Nafion

NAFION 501 resin, the potassium salt of the tetrafluoroethylenesulfonly floride vinyl ether copolymer, was exchanged with 20% nitric acid at 20° C. for 24 hours. The acid form "H-Nafion" obtained was washed with deionized water and subsequently dried overnight at 150° C.

EXAMPLE 1

Amination of propylene and isobutylene were carried out in a tubular micro reactor. 4 c.c. of H-Nafion granules were used in a stainless steel tubular reactor 10 inches long and ¼" in diameter. The catalyst was heated in helium up to 150° C. The reactants ammonia followed by isobutylene or propylene were introduced over the catalyst giving an ammonia to isobutylene ratio varying from 1 to 4. No appreciable reaction was observed until a temperature of about 220° C. was reached. The reaction conditions studied were:

| | |
|---|---|
| Temperature (°C.) | 200–250 |
| Pressure | 765 psig |
| GHSV | 1,000–1,500 |

The reactants and products were analyzed using an on-line gas chromatograph. The results of aminated isobutylene and propylene as described above are shown in Table 1 along with results for the same reaction under the same conditions using silica-alumina and H-mordenite catalysts.

TABLE I

PROPYLENE AND ISOBUTYLENE AMINATION OVER H—NAFION, SILICA-ALUMINA, AND H—AND MORDENITE OLEFIN AMINATION

| Run | Catalyst | Olefin | Temp. C. | P(psia) | GHSV | N/R | % Conv |
|---|---|---|---|---|---|---|---|
| 1 | N—Nafion | Isobutylene | 220 | 765 | 1450 | 2 | 0.40 |
| 2 | H—Nafion | Isobutylene | 220 | 765 | 1000 | 2 | 0.51 |
| 3 | H—Nafion | Isobutylene | 240 | 765 | 1000 | 2 | 2.1 |
| 4 | H—Nafion | Isobutylene | 240 | 765 | 1000 | 1 | 1.8 |
| 5 | H—Nafion | Isobutylene | 250 | 765 | 1000 | 2 | 3.0 |
| 6 | H—Nafion | Propylene | 220 | 765 | 2000 | 4 | 0.2 |
| 7 | Silica-Alumina | Isobutylene | 220 | 765 | 1000 | 2 | 0.5 |
| 8 | Silica-Alumina | Isobutylene | 240 | 765 | 1000 | 2 | 1.9 |
| 9 | Silica-Alumina | Isobutylene | 250 | 765 | 1000 | 2 | 2.7 |
| 10 | Silica-Alumina | Isobutylene | 260 | 765 | 1000 | 2 | 5.0 |
| 11 | Silica-Alumina | Propylene | 240 | 765 | 1000 | 2 | 0 |
| 12 | H—Mordenite Z-900H | Isobutylene | 220 | 765 | 1000 | 2 | 0.9 |
| 13 | H—Mordenite Z-900H | Isobutylene | 240 | 765 | 1000 | 2 | 2.9 |
| 14 | H—Mordenite Z-900H | Isobutylene | 260 | 765 | 1000 | 2 | 5.9 |

Comparing the conversions obtained using H-Nafion, runs 1–6, with the conversions obtained using silica-alumina or H-Mordenite, runs 7–11 and 12–14 respectively, it can be seen that H-Nafion is a suitable catalyst for olefin amination. While the amination of isobutylene is comparable for both H-Nafion and the prior art catalysts, some conversion of propylene was found with H-Nafion whereas none was observed with silica-alumina; see runs 6 and 11.

In addition to amination of propylene, H-Nafion has the added advantage over the prior art silica-alumina and alkali metal catalysts in that there is no maximum size limit for olefins which can be aminated.

Also, unlike amination reactions using metal supported catalysts, the present invention provides for the formation of amine products without the formation of nitriles.

Having thus described the present invention, what is now deemed appropriate for Letters Patent is set out in the following appended claims:

1. A process for forming an amine which comprises: reacting ammonia, a primary amine, or a secondary amine with an olefin, under conditions effective for forming said amine, in the presence of an effective amount of an organic acid catalyst wherein said organic acid catalyst is perfluorinated and has a Hammett acidity value no greater than about −10.

2. The process in accordance with claim 1 wherein said olefin is isobutylene.

3. The process in accordance with claim 1 wherein said organic acid catalyst has a Hammett acidity value no greater than about −15.

4. The process in accordance with claim 3 wherein said organic acid catalyst is a solid Cation exchange resin with at least one sulfonic acid functional group.

5. The process is accordance with claim 4 wherein said reaction is carried out in the gas phase at a temperature between 200° to 250° C. and a pressure between 400 to 2,000 psig.

6. A process for aminating an olefin with ammonia, a primary amine or a secondary amine, which process comprises carrying out said amination in the presence of a perfluorinated organic solid cation exchange resin having a repeating structure of the general formula:

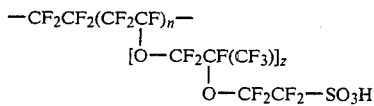

where: n=15–20 and z=1 or 2

7. The process in accordance with claim 6 wherein said reaction is carried out in the vapor phase at a temperature between 200° to 250° C.

8. The process in accordance with claim 7 wherein the amine to olefin mole ratio for the reaction is between 1:1 to 2:1.

9. The process in accordance with claim 8 wherein said amination is run at a gas hourly space velocity between 500 to 2,000.

10. The process in accordance with claim 9 wherein said reaction is carried out at a pressure between 400 to 2,000 psig.

11. The process in accordance with claim 10 wherein said olefin is isobutylene.

* * * * *